United States Patent [19]

Leighton

[11] Patent Number: 5,085,631
[45] Date of Patent: Feb. 4, 1992

[54] METHOD AND KIT FOR ADMINISTERING SPINAL SUBARACHNOID ANESTHESIA

[75] Inventor: Barbara Leighton, Philadelphia, Pa.

[73] Assignee: Thomas Jefferson University, Philadelphia, Pa.

[21] Appl. No.: 488,467

[22] Filed: Feb. 26, 1990

Related U.S. Application Data

[63] Continuation of Ser. No. 227,409, Aug. 2, 1988, abandoned.

[51] Int. Cl.$^5$ .............................................. A61M 19/00
[52] U.S. Cl. ..................................... 604/28; 604/158; 604/164
[58] Field of Search ..................... 604/28, 36, 38, 158, 604/164, 165, 181, 187, 239, 264, 272, 280; 128/748, 760

[56] References Cited

U.S. PATENT DOCUMENTS

| | | | |
|---|---|---|---|
| 2,922,420 | 1/1960 | Cheng | 128/DIG. 16 |
| 3,081,770 | 3/1963 | Hunter | 604/33 |
| 3,672,367 | 6/1972 | Scislowicz . | |
| 3,780,733 | 12/1973 | Martinez-Manzor | 604/158 |
| 3,788,320 | 1/1974 | Dye | 604/165 |
| 3,792,703 | 2/1974 | Moorehead . | |
| 4,068,659 | 1/1978 | Moorehead . | |
| 4,406,656 | 9/1983 | Hattler et al. | 604/158 |
| 4,518,383 | 5/1985 | Evans | 604/164 |
| 4,529,399 | 7/1985 | Groshong et al. | 604/53 |
| 4,645,491 | 2/1987 | Evans | 604/158 |
| 4,721,506 | 1/1988 | Teves | 604/158 |
| 4,737,146 | 4/1988 | Amaki et al. | 604/158 |
| 4,808,157 | 2/1989 | Coombs | 604/158 |
| 4,917,670 | 4/1990 | Hurley et al. | 604/51 |

OTHER PUBLICATIONS

Krueger, "Etiology of Treatment of Postspinal Headaches", *Current Researches in Anesthesia and Analgesia*, pp. 190-198 (May-Jun. 1953).
Vandam et al., "Long-Term Follow-Up of Patients Who Received 10,098 Spinal Anesthetics", *J.A.M.A.*, 161(7):586-591 (1956).
Harris et al., "The Comparative Incidence of Postlumbar Puncture Headache Following Spinal Anesthesia Administered Through 20 and 24 Gauge Needles", *Anesthesiology* 14:390-397 (Jul. 1953).
Hurley et al., "New Microcatheter Technique Reduces Anesthetic Needs", *Anesthesiology News*, pp. 12-13, (Oct. 1987).
Greene, "A 26 Gauge Lumbar Puncture Needle: Its Value in the Prophylaxis of Headache Following Spinal Analgesia for Vaginal Delivery", *Anesthesiology*, 11:464-469 (Jul. 1950).
Hurley et al., "Continuous Spinal Anesthesia with a Micro-Catheter Technique", *ARSA 12th Annual Meeting Abstracts*, 12(1):53-54 (Jan.-Mar. 1987).
Sihota et al., "Post-Spinal Headache After Continuous Subarachnoid Anesthesia: A Prospective Data-Based Study", *ARSA 12th Annual Meeting Abstracts*, 12(1):54-55 (Jan.-Mar. 1987).

(List continued on next page.)

*Primary Examiner*—Stephen C. Pellegrino
*Assistant Examiner*—Glenn K. Dawson
*Attorney, Agent, or Firm*—Woodcock Washburn Kurtz Mackiewicz & Norris

[57] ABSTRACT

A method for administering spinal subarachnoid anesthesia to a patient is disclosed. The method includes the steps of: (a) providing an introducer assembly having an outer epidural needle having a distal tip, an inner subarachnoid needle having a distal tip, and a spinal subarachnoid catheter slidingly disposed around the inner subarachnoid needle and positioned within the outer epidural needle, the catheter having a distal tip and a proximal tip; (b) introducing the epidural needle into an epidural space until the distal tip of the epidural needle is in close proximity to the dural membrane; (c) advancing the subarachnoid catheter and subarachnoid needle through the epidural needle until the dural membrane is fully penetrated by the distal tip of the catheter and the distal tip of the subarachnoid needle; (d) withdrawing the subarachnoid needle from within the catheter while leaving the catheter in place; and (e) introducing anesthesia into the spinal subarachnoid space through the proximal tip of the catheter to anesthetize the patient. A kit for the subarachnoid catheter delivery of anesthesia is also described.

14 Claims, 3 Drawing Sheets

OTHER PUBLICATIONS

A commercial brochure advertising different epidural anesthesia devices published by Baxter.

Bridenbaugh et al., "Spinal, Subarachnoid Neural Blockade", *Neural Blockade in Clinical Anesthesia and Management of Pain*, eds. J. B. Lippincott (1980) pp. 161-162.

Huckaby et al., "Applications of Continuous Spinal Anesthesia with a New Micro-Catheter for Obstetrics: Patient Acceptance and Satisfaction", *Society for Obstetric Anesthesia and Perinatology 20th Annual Meeting Abstracts*, p. 29 (Apr. 27-30, 1988).

J. J. Bonica, "Postspinal Complications", *Obstetrical Anesthesia: Current Concepts and Practice*, S. M. Shnider ed. Williams & Wilkins, Baltimore (1970), p. 175.

R. J. Munhall et al., "Incidence and Etiology of Failed Spinal Anesthetics in a University Hospital: A Prospective Study", *Anesth. Analg.*, 67:843-8, (1988).

A. P. Winnie, "An 'Immobile Needle' for Nerve Blocks", *Anesthesiology*, vol. 31, No. 6, 577-578, Dec. 1969.

P. T. Schlake et al., "Separation of the Hub from the Shaft of a Disposable Epidural Needle", *Anesthesiology*, 68(4): Apr. 1988, pp. 611-613.

A. P. Winnie, "A Grip to Facilitate the Insertion of Epidural Needle", *Anesthesia and Analgesia*, 50(1):23-25, (Jan.-Feb. 1971).

E. Grundy et al., "Comparison of Spread of Epidural Anesthesia in Pregnant and Nonpregnant Women", *Anesth. Analog.*, 57:544-546, 1978.

METHOD AND KIT FOR ADMINISTERING SPINAL SUBARACHNOID ANESTHESIA

This is a continuation of application Ser. No. 227,409, filed Aug. 2, 1988, now abandoned.

BACKGROUND OF THE INVENTION

Presently, two types of spinal anesthesia techniques are routinely employed in surgical and/or child birth procedures. The two techniques are epidural anesthesia and subarachnoid anesthesia. With epidural anesthesia, a catheter is usually placed in the spinal epidural space and anesthesia is administered through the catheter. This technique has the advantage of providing for administration over an extended period of time, however, there are certain disadvantages related to the administration of anesthesia into this space. One such disadvantage is the non-uniform and often unpredictable distribution of the anesthesia. This distribution problem is due to the nature of the tissue in the epidural space, which is a tissue composed of primarily fatty and fibrous materials rather than free-flowing fluid.

A number of systems have been suggested for placing catheters, including some used for epidural anesthesia. U.S. Pat. No. 4,645,491 (Evans), discloses one such system particularly designed for spinal injection. Also refer to U.S. Pat. No. 3,672,367 (Scislowicz); 3,792,703 (Moorehead); 4,068,659 (Moorehead); 4,406,656 (Hattler et al); and 4,529,399 (Groshong et al), all disclosing devices for placing catheters wherein a stylet is position within the catheter and the catheter is positioned within a piercing needle. In U.S. Pat. No. 3,792,703 (Moorehead), for example, a system is disclosed where an intravenous catheter is introduced through a larger introducer needle. Within the bore of the catheter is a rigid tube which can be advanced with the catheter upon insertion. In U.S. Pat. No. 4,068,659 (Moorehead) an unhubbed intravenous catheter with a conventional stylet is passed through a sheath and an introducer needle. The stylet has a distal wing-tip to aid catheter passage. The catheter is adapted to later receive a needle hub.

Because the subarachnoid space is far more liquified, and thereby a faster, more uniform and more predictable distribution medium, catheter delivered administration of anesthesia directly into the spinal subarachnoid space would be preferable for most surgeries and child birth procedures, were it not for one major side effect that is often associated with such administrations. The major problem is the severe post-operative headaches that often result from the puncture of the dural membrane (or dura), the barrier or membrane surrounding the spinal subarachnoid space, upon entrance of the relatively large conventional catheter-delivery anesthesia devices into the subarachnoid area.

Studies have been conducted which correlate the size of the puncture in the dural membrane to the severity of the headaches experienced by patients. In J. J. Bonica, "Postspinal Complications, *Obstetrical Anesthesia: Current Concepts and Practice*, SM Shnider, ed. Williams & Wilkins, Baltimore (1970) at page 175 the incidence of postpuncture headache was correlated to both needle size and bevel. Earlier, Krueger had correlated headache incidence with needle tip configuration for 20 gauge needles (beveled vs. pencilpoint). Krueger, "Etiology of Treatment of Postspinal Headaches", *Current Researches in Anesthesia and Analgesia*, pp 190–198 (May–June 1953). It is for these reasons that when epidural catheters are placed, efforts are normally taken to ensure that they do not rupture this dural membrane. Such efforts include, for example, using bent epidural introducer needles which tend to direct the catheter away from the dura, thereby minimizing the probability of puncture. See also Vandam et al, "Long-Term Follow-Up of Patients Who Received 10,098 Spinal Anesthetics", *J.A.M.A.* 161(7):586–591 (1956).

Thus, when subarachnoid anesthesia is employed, a catheter-based system is generally not used. Instead, a smaller straight needle is passed through the epidural space and the dural membrane into the cerebrospinal fluid, and a bolus injection of anesthesia is administered. Various methods for introducing small needles to deliver subarachnoid anesthetic have been suggested. In Harris et al, The Comparative Incidence of Postlumbar Puncture Headache Following Spinal Anesthesia Administered Through 20 and 24 Gauge Needles", *Anesthesiology* 14:390–397 (July, 1953) improvement was noted when a smaller 24 gauge needle was used instead of a 20 gauge needle. Harris et al employed a technique where a three and one half inch 24 gauge needle was inserted through a 2 inch 20 gauge introducer.

Greene, "A 26 Gauge Lumbar Puncture Needle: Its Value in the Prophylaxis of Headache Following Spinal Analgesia For Vaginal Delivery", *Anesthesiology*, 11:464–469 (July, 1950) described a similar "double needle" technique using a 26 gauge 10 cm. long spinal needle introduced through a 21 gauge 5 cm. long needle, both needles complete with their own stylets. According to Greene's technique, the 21 gauge needle with its stylet in place is introduced through the subcutaneous tissues until a plane of increased resistance is felt. The point of the needle is then reported to be within 1 cm. of the dura. The stylet is removed and the 26 gauge needle, with or without its wire stylet in place, is passed through the introducer to puncture the dura mater easily. The results of this procedure are said to prevent the high incidence of postpuncture headache encountered in the use of spinal analgesia for vaginal delivery.

A number of different needle guides and introducers are currently available for use in introducing small (25-26) gauge needles. These introducers aid in the direction of the needles, and reduce the incidence of coring and of introducing pieces of epidermis or bacteria into the subarachnoid space. The needles themselves are available with various tip configurations, non-cutting bevels or pencil point types being generally preferred.

Obviously, one disadvantage of using a needle injected bolus of subarachnoid anesthesia is that it lasts generally no more than a few hours. If the procedure lasts longer than the anesthetic bolus, spinal anesthesia is generally abandoned and resort is made to another anesthetic process.

The ideal delivery technique, therefore, would be one which provides for intermittent or continuous delivery of anesthesia, while at the same minimizing the degree and incidence of dural membrane rupture.

Recently, the use of a relatively small subarachnoid needle internally threaded with an even smaller (32 gauge) catheter was reported for administration of subarachnoid anesthesia. Hurley et al, "Continuous Spinal Anesthesia With a Microcatheter Technique", *ASRA 12th Annual Meeting Abstracts*, 12(1):53–54 (January–March 1987); Hurley et al, "New Microcatheter Technique Reduces Anesthetic Needs", *Anesthesiology News*, pp. 12-13 Oct. 1987. Using this technique, the needle is used to puncture the dura, and a catheter is inserted through the inner bore of the needle into the spinal subarachnoid space. The needle is then withdrawn leaving the catheter in place. There are, however, several problems with this insertion technique. For one, the catheter tends to fall out of the hole which is created by the larger needle since the dural membrane is not sufficiently elastic to return in part to its original position and hold the smaller catheter firmly in place. Secondly, the size of the catheter employed inside the needle is so small that it easily develops kinks. In addition, the small size of the needle results in rates of administration that are only between about ½ to 1 cc per minute. Since the normal dose of spinal anesthetic is approximately 1 to 3 cc, an anesthesiologist with excellent hand strength (for forcing the syringe) would thus be required to spend up to three minutes on administering the anesthesia alone. In essence, this system is merely a miniaturization of existing epidural catheter placement techniques, and one that does not adequately solve the unfulfilled and long-felt need for a better subarachnoid anesthesia technique.

Although unrelated to catheters used for administration of anesthesia, techniques are known for introducing catheters into vascular systems. One such technique is commonly used for introducing intra-venous (IV) catheters. Under this system, the catheter is positioned around the outside of a needle, and terminates in a taper immediately behind the tip of the needle at its distal end. At its proximal end a hub is employed to hold the catheter in place as the needle which it surrounds is withdrawn from the vein. The placement of IV catheters in veins which are quite close to the surface, thus requiring very little catheter passage through tissue before the needle and catheter tip enter the target vein, makes the concerns present there different from the concerns applicable to placement of catheters for spinal anesthesia.

New and better systems for supplying anesthesia, particularly supplying anesthesia to the spinal subarachnoid space, are needed. The present invention is directed to this end.

SUMMARY OF THE INVENTION

The present invention is directed to a novel method and kit for administering spinal subarachnoid anesthesia to a patient. It provides for a relatively high rate of intermittent bolus or continuous delivery of anesthesia to the subarachnoid area while at the same time minimizing the degree and incidence of dural membrane rupture, thereby overcoming significant disadvantages of currently used art processes. Use of the present invention should result in a decrease in the risk of postoperative spinal headaches and provide a more effective spinal anesthesia technique than heretofore known.

Specifically, the invention provides a method of administering anesthesia to a patient, comprising the steps of: (a) providing an introducer assembly, said introducer assembly comprising (i) an outer epidural needle comprising a distal tip, (ii) an inner subarachnoid needle comprising a distal tip, and (iii) a spinal subarachnoid catheter slidingly disposed around said inner subarachnoid needle and slidingly positioned within said outer epidural needle, said catheter comprising a distal tip and a proximal tip; (b) introducing said epidural needle into an epidural space until said distal tip of said epidural needle is in close proximity to a dural membrane; (c) advancing said subarachnoid catheter and subarachnoid needle through said epidural needle until said dural membrane is fully penetrated by said distal tip of said catheter and said distal tip of said subarachnoid needle; (d) withdrawing said subarachnoid needle from within said catheter while leaving said catheter in place; and (e) introducing anesthesia into a spinal subarachnoid space through said proximal tip of said catheter to anesthetize said patient. In the preferred method, the epidural needle is removed from around the catheter while leaving the catheter in place. This epidural removal step should be performed at some point following step (c) and preceding step (e).

In addition, the present invention encompasses a spinal subarachnoid catheter-delivered anesthesia kit, comprising: an epidural needle; a subarachnoid catheter sized for introduction through said epidural needle, said subarachnoid catheter comprising a proximal tip; and a subarachnoid needle, said subarachnoid needle being sized for slidingly engaging the interior of said catheter and comprising both a distal tip suitable for penetrating a dural membrane and a proximal tip.

Preferably, the distal tip of the subarachnoid needle is a pencil-point tip. In addition, the catheter preferably has a gauge of between about 20 and 28, most preferably about 24, and the subarachnoid needle and the catheter have a length of at least about 50 cm, preferably 70 cm or more. Also preferred is an embodiment wherein the subarachnoid needle further comprises a syringe hub at the proximal tip of the needle.

These and other features of the subject invention will be apparent from the following detailed description of preferred embodiments of the subject invention read with reference to the accompanying drawings.

DETAILED DESCRIPTION OF PREFERRED EMBODIMENTS

Figure 1:
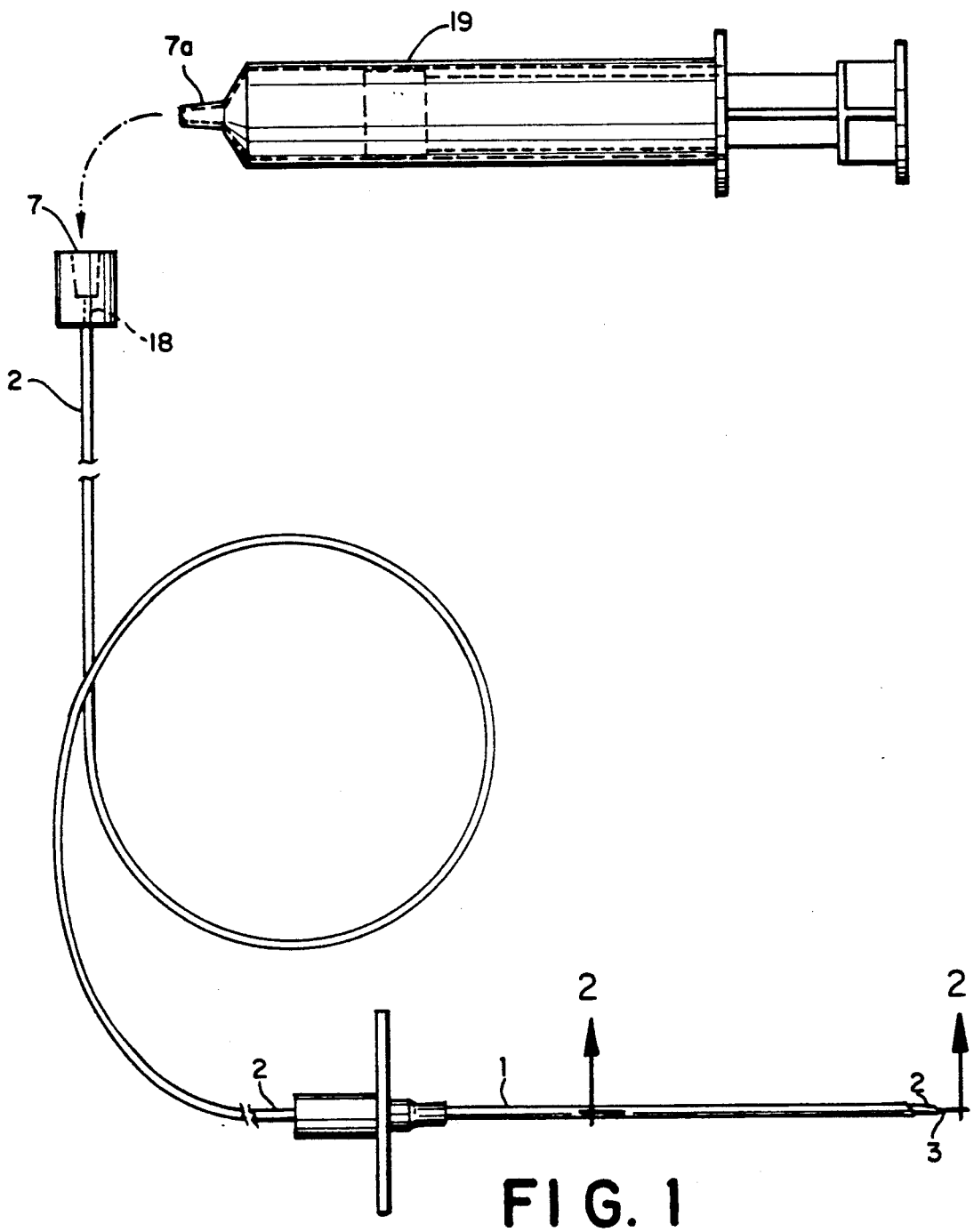
FIG. 1 is a diagrammatic view of the introducer assembly, showing the outer epidural needle, the inner subarachnoid needle and the spinal subarachnoid catheter.
Figure 2:
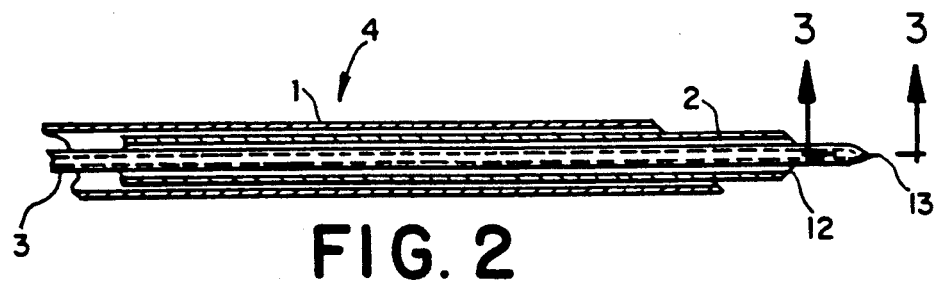
FIG. 2 is an enlarged sectional view of the introducer assembly taken along line 2—2 of FIG. 1.

As depicted in the Figures, the present invention provides a novel method of administering anesthesia to a patient, as well as a kit for subarachnoid catheter delivery.

The patient can be any vertebrate, but most preferably is a human patient. The method of the invention is carried out by utilizing introducer assembly 4. Assembly 4 includes outer epidural needle 1, inner subarachnoid needle 3 and spinal subarachnoid catheter 2. The subarachnoid needle has a permanent needle hub 7 disposed at its proximal end 18. The end of the catheter 2 abuts this hub, so that advancement of the subarachnoid needle will also advance the catheter. As depicted in FIGS. 2 and 4(a)-(e), catheter 2 is slidingly disposed around inner subarachnoid needle 3 and slidingly positioned within outer epidural needle 1. In practicing the method of the invention, epidural needle 1 is introduced into epidural space 5 by advancing through epidermal membrane 20 and ligamentous tissue 8 of spinal region 9 using standard epidural placement techniques. During the initial advancement of the epidural needle 1, neither the catheter 2 nor subarachnoid needle 3 need be in place. At the physician's discretion, a conventional stylet may be used during this phase of the procedure.

Figure 5:
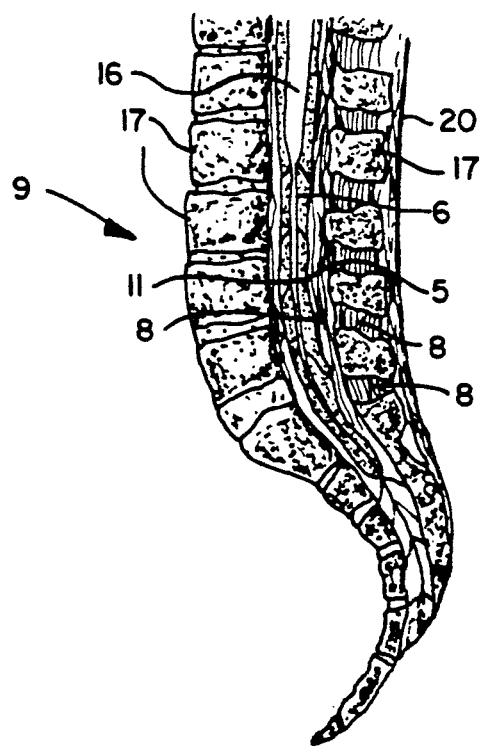
FIG. 5 is a diagrammatic, cross sectional view of the spinal region.
Figure 4A:
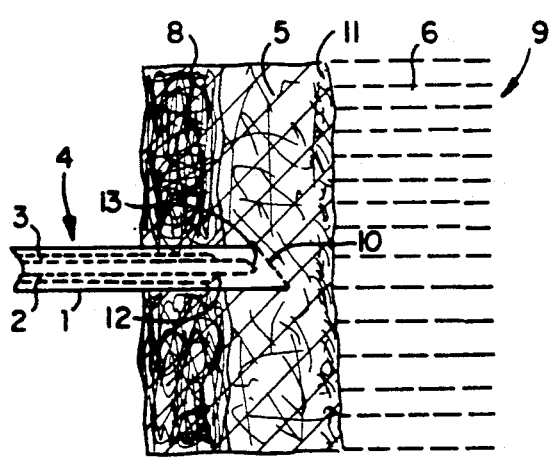
FIG. 4 is a diagrammatic sectional view of the introducer assembly and a segment of the spinal region depicting various insertional stages of the assembly in this region; for purposes of illustration in this Figure, the epidural space is illustrated as being much wider relative to the bevel of the epidural needle than in actual practice.

FIG. 5 provides an overall picture of the spinal region 9 showing spinal cord 16, dural membrane 11, ligamentous tissue 8, bone tissue 17, epidural space 5, and the ultimate target of the present invention, spinal subarachnoid space 6. The distal tip 10 of epidural needle 1 is now in close proximity to dural membrane 11, as shown in FIG. 4(a). The epidural space is very thin (4-6 mm). It is capable of containing the entire distal tip of the epidural needle, but is not much wider than the epidural needle tip. The width of the epidural space is greatly exaggerated in the drawings for purposes of illustration. In any event, the epidural needle is not advanced further once the epidural space is reached.

Figure 4B:
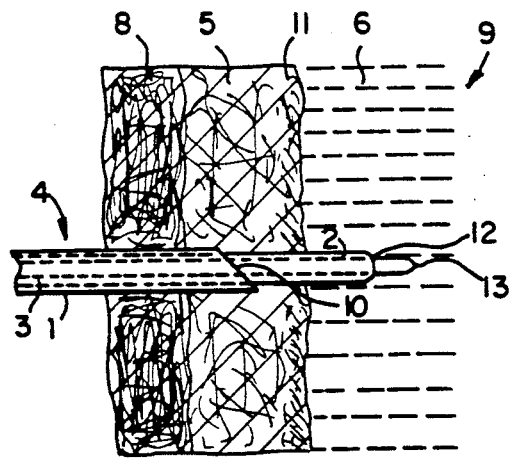
Figure 4C:
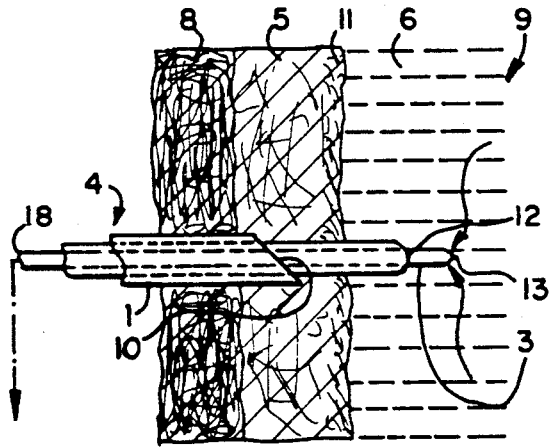
Figure 4D:
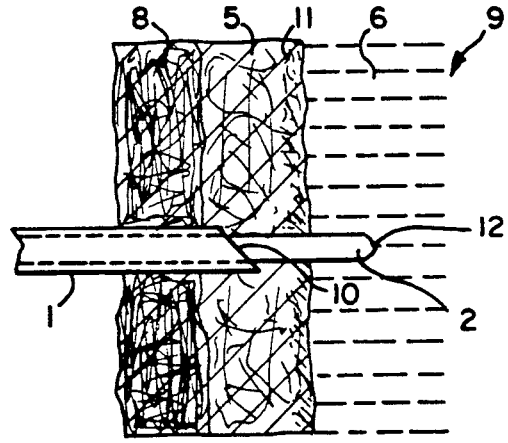
Figure 4E:
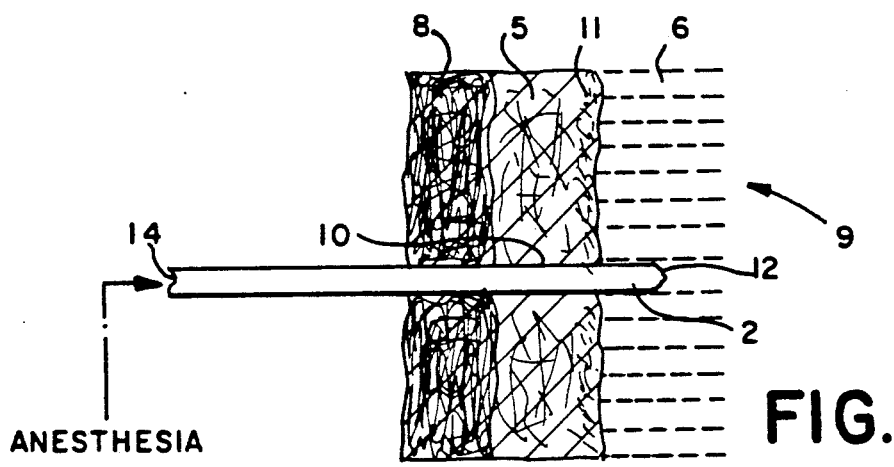

The larger epidural needle 1 serves to protect the somewhat delicate catheter 2 that could otherwise be badly damaged by passage through the ligamentous tissue 8. The subarachnoid catheter 2 and inner subarachnoid needle 3 are then slidingly advanced through the epidural needle 1 until dural membrane 11 is fully penetrated by a distal tip 12 of catheter 2 and distal tip 13 of subarachnoid needle 3, as illustrated in FIG. 4(b). Confirmation that the dural membrane has been penetrated may be made by withdrawing cerebrospinal fluid from the subarachnoid space, as shown in FIG. 4(c). This withdrawal step utilizes the subarachnoid needle 3, its hub 7 and a conventional syringe, such as syringe 19 connected through tip 7a to hub 7. As depicted in FIG. 4(d), the subarachnoid needle 3 is then slidingly withdrawn from within the catheter 2, leaving catheter 2 in place. The epidural needle 1 may also be slidingly withdrawn from around catheter 2, either before or after withdrawal of the subarachnoid needle, leaving catheter 2 in place. Anesthesia may then be introduced, in a single dose, intermittently or continuously, into spinal subarachnoid space 6 through proximal tip 14 of spinal subarachnoid catheter 2, as generally shown in FIG. 4(e). In carrying out anesthesia introduction, a removable syringe hub (not shown in the Figures) is placed on or around proximal tip 14 of catheter 2. Syringe 19 is then employed in a conventional fashion to effect anesthesia introduction.

As one skilled in the art will recognize, this invention is particularly useful when the need for anesthesia is long or unpredictable, such as in child birth or lower extremity vascular or orthopedic surgery. It would also have applications in continuous infusion of lipid soluble narcotics (such as fentanyl and its derivatives) for post-operative pain relief. Such lipid soluble narcotics provide better pain relief and have fewer side effects than water soluble narcotics, but have a short duration of action and therefore are currently only used epidurally for post-operative pain relief.

If desired, and in fact preferred, outer epidural needle 1 may be withdrawn from around catheter 2 after distal tip 12 of catheter 2 and distal tip 13 of subarachnoid needle 3 are advanced through and have penetrated dural membrane 11, leaving catheter 2 and subarachnoid needle 3 in place. Alternatively, if desired, epidural needle 1 may be withdrawn from around catheter 2 after inner subarachnoid needle 3 has been withdrawn from within catheter 2. In either event, the epidural needle is removed from around the subarachnoid catheter at some time before anesthesia is administered, for the epidural needle must be removed before hub 7 can be attached to catheter 2.

As an additional procedure, one may aspirate fluid from spinal subarachnoid space 6, generally termed cerebrospinal fluid, through subarachnoid needle 3, after distal tip 12 of subarachnoid catheter 2 and distal tip 13 of subarachnoid needle 3 are advanced through and have penetrated dural membrane 11. This procedure is generally shown in FIG. 4(c). Preferably, the subarachnoid needle 3 has a permanent hub 7 at its proximal end 18 for use during aspiration. This hub does not interfere with the ability to remove the epidural needle 1 before the subarachnoid needle 3. Syringe 19 is employed in a conventional manner to effect aspiration. The aspirated fluid flows into aperture 15 of distal tip 13 and out proximal tip 18 of inner subarachnoid needle 3. Using this system, the correct placement of catheter 2 in spinal subarachnoid space 6 can be easily confirmed.

The invention also includes a spinal subarachnoid catheter-delivered anesthesia kit, comprising outer epidural needle 1, a spinal subarachnoid catheter 2 and an inner subarachnoid needle 3. Subarachnoid catheter 2 is sized for introduction through the epidural needle 1 and comprises proximal tip 14 as best shown in FIGS. 2 and 4(a)-(e). Subarachnoid needle 3 is sized for slidingly engaging the interior of catheter 2 and comprises a distal tip 13 suitable for penetrating dural membrane 11 as depicted in FIG. 4.

Figure 3:
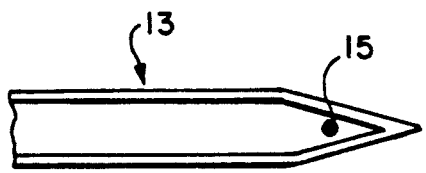
FIG. 3 is an enlarged view of the distal tip of the inner subarachnoid catheter taken along line 3—3 of FIG. 2.

Although any conventional distal tip 13 of inner subarachnoid needle 3 may be employed in the subject invention, the preferable distal tip 13 is a pencil-point tip such as is shown in FIG. 3. FIG. 3 depicts distal tip 13 with distally placed aperture 15.

The preferable diameter for catheter 6 is between about gauge 20 and gauge 28. Most preferably, catheter 6 has a diameter of about gauge 24. The preferable length for catheter 6 and subarachnoid needle 3 is approximately 70 cm.

Using the novel procedure and kit disclosed herein, one is able to catheterize the subarachnoid space, thus permitting additional anesthesia dosing during the course of childbirth or surgical procedure, without further puncturing of the dura. Moreover, since the catheter has been introduced on the outside of the puncturing needle, it will not have a tendency to fall out. Further, the size of catheter relative to the size of dural membrane puncture is maximized using this technique, thereby maximizing flow. A corresponding reduction in the incidence of post-operative headache should result from use of this system.

What is claimed is:

1. A method of administering spinal anesthesia to a patient, comprising the steps of:
   (a) providing an introducer assembly comprising at least three components, said three components including:
      (i) an outer epidural needle having a distal tip;
      (ii) an inner subarachnoid needle having a distal tip; and
      (iii) a spinal subarachnoid catheter closely approximated to and slidingly disposed around said inner subarachnoid needle and slidingly positioned within said outer epidural needle, said catheter comprising a distal tip and a proximal tip;

(b) introducing said epidural needle into an epidural space until said distal tip of said epidural needle is in close proximity to a dural membrane;

(c) advancing said subarachnoid catheter and subarachnoid needle through said epidural needle until the dural membrane is fully penetrated by said distal tip of said catheter and said distal tip of said subarachnoid needle;

(d) withdrawing said subarachnoid needle from within said catheter while leaving said catheter in place;

(e) withdrawing said epidural needle from around said catheter; and (f) introducing anesthesia into a spinal subarachnoid space through said proximal tip of said catheter to anesthetize said patient.

2. The method of claim 1 further comprising aspirating cerebrospinal fluid through said subarachnoid needle following step (c) to confirm that said dural membrane has been penetrated.

3. The method of claim 1 wherein said distal tip of said subarachnoid needle is a pencil-point tip.

4. The method of claim 1 wherein said catheter is selected to have a gauge between about 20 and 28.

5. The method of claim 4 wherein said catheter is selected to have a gauge of about 24.

6. The method of claim 1 wherein said subarachnoid needle and said catheter are selected to be at least about 70 cm long.

7. The method of claim 1 wherein in step (c) said catheter and said subarachnoid needle are advanced in unison.

8. The method of claim 1 wherein said subarachnoid needle further comprises a syringe hub at said proximal tip of said subarachnoid needle.

9. A spinal subarachnoid catheter-delivered anesthesia kit, comprising at least three components, said three components including:

(a) an epidural needle having a distal tip;

(b) a subarachnoid catheter sized for introduction through said epidural needle, said subarachnoid catheter comprising a proximal tip; and (c) a subarachnoid needle, said subarachnoid needle being sized for slidingly engaging the interior of said catheter, and comprising a distal tip suitable for penetrating a dural membrane and a proximal tip.

10. The kit of claim 9 wherein the distal tip of said subarachnoid needle is a pencil-point tip.

11. The kit of claim 9, wherein said subarachnoid catheter is selected to have a gauge of between about 20 and 28.

12. The kit of claim 11 wherein said catheter is selected to have a gauge of about 24.

13. The kit of claim 9 wherein said subarachnoid needle and said catheter are selected to be at least about 70 cm long.

14. The kit of claim 9 wherein said subarachnoid needle further comprises a syringe hub at said proximal tip.

* * * * *